United States Patent
Underdown et al.

(10) Patent No.: US 10,743,863 B2
(45) Date of Patent: Aug. 18, 2020

(54) PERFECT CLOSURE SURGICAL NEEDLE

(71) Applicants: Teresa R Underdown, Wickenburg, AZ (US); Gary D Kaufman, Scottsdale, AZ (US)

(72) Inventors: Teresa R Underdown, Wickenburg, AZ (US); Gary D Kaufman, Scottsdale, AZ (US)

(*) Notice: Subject to any disclaimer, the term of this patent is extended or adjusted under 35 U.S.C. 154(b) by 408 days.

(21) Appl. No.: 15/425,945

(22) Filed: Feb. 6, 2017

(65) Prior Publication Data
US 2018/0221019 A1    Aug. 9, 2018

(51) Int. Cl.
*A61B 17/06*    (2006.01)

(52) U.S. Cl.
CPC .. *A61B 17/06066* (2013.01); *A61B 17/06004* (2013.01); *A61B 2017/0608* (2013.01); *A61B 2017/06028* (2013.01)

(58) Field of Classification Search
CPC .......... A61M 2205/192; A61M 5/3286; A61B 2017/0608; A61B 17/06004; A61B 17/06066; A61B 2017/3454
USPC ................................................ 604/273, 274
See application file for complete search history.

(56) References Cited

U.S. PATENT DOCUMENTS

| | | | | |
|---|---|---|---|---|
| 3,038,475 A * | 6/1962 | Orcutt | ..................... | B21G 1/08 606/223 |
| 3,094,123 A * | 6/1963 | Kurtz | ..................... | A61B 17/06 606/223 |
| 4,128,351 A * | 12/1978 | Kurtz | ............... | A61B 17/06066 30/168 |
| 4,527,564 A * | 7/1985 | Eguchi | ............. | A61B 17/06066 606/145 |
| 5,749,897 A * | 5/1998 | Matsutani | ........ | A61B 17/06066 163/5 |
| 6,124,030 A * | 9/2000 | Suzuki | ..................... | G11B 5/41 428/328 |
| 8,062,332 B2 * | 11/2011 | Cunningham | ... | A61B 17/06066 606/222 |
| 2010/0016811 A1 * | 1/2010 | Smith | ................ | A61B 17/3417 604/273 |

* cited by examiner

*Primary Examiner* — Matthew F DeSanto

(57) ABSTRACT

This surgical needle may reduce unwanted and unanticipated tissue distortion and/or tearing and undesirable scar tissue during wound healing. The surgical needle will guide tissue separation more properly along planes of tissue stress, minimizing tissue distortion and improving tissue apposition.

1 Claim, 2 Drawing Sheets

FIG 5
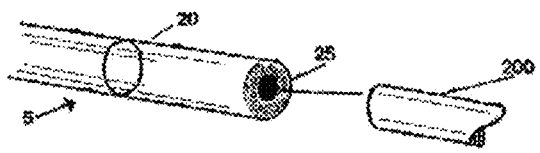
FIG 6
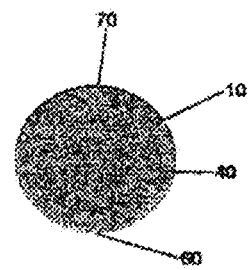
FIG 7
FIG 8
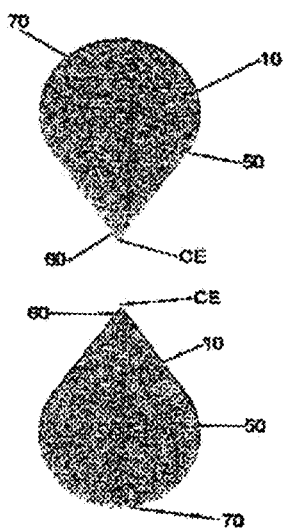
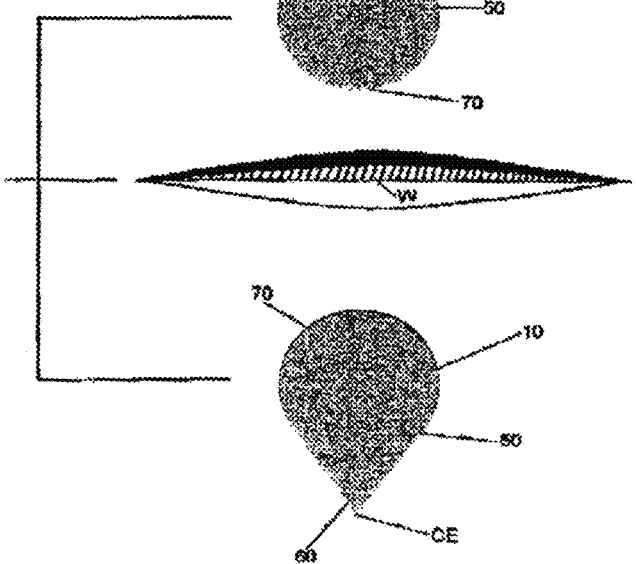

PERFECT CLOSURE SURGICAL NEEDLE

FIELD OF THE INVENTION

The present invention relates generally to improved surgical needles. More specifically the present invention relates to surgical needles that reduce unwanted and unanticipated tissue distortion and/or tearing and the subsequent increase in undesirable scar tissue during wound healing. More specifically, a surgical needle that will guide tissue separation more properly along planes of tissue stress, minimizing tissue distortion and improving tissue apposition.

BACKGROUND OF THE INVENTION

Surgical needles are well known in the medical field. They are generally grouped into two categories: (1) Taper point and (2) Cutting edge, based on needle configuration. In general, taper point needles are used to penetrate thin or soft tissue such as intestinal or muscle tissue, whereas cutting edge needles are used in thicker or denser tissue such as skin or cartilage or any other tissue that is more dense and difficult to penetrate. Both taper point and cutting edge needles come with advantages and disadvantages. While taper point needles do not slice tissue, they can be very difficult or impossible to pass, especially in the denser tissue. In addition they will separate tissue obviously along planes of tissue weakness and these planes may be in an undesirable direction of separation or tear, for example toward or into the wound edge. Cutting edge needles as they are now conformed necessarily slice tissue. While this allows for needle passage in a dense tissue, the slices are in three planes, two of which are parallel to the incision or wound edge and a third plane which is slicing tissue toward the incision or wound edge as with a cutting edge needle, or a third plane directed directly away from the incision or wound edge as with the reverse cutting edge needle design.

Conventional cutting edge needles to date, even with the reverse cutting edge design result in tissue slices that allow and promote tissue gaping at the penetration site, especially with increased tension on the placed suture either from tissue tension during closure or from post-operative swelling.

There is a need in this art for a needle that can penetrate all tissues, both weak and easily distortion from tension placed on the tissue during suture placement and/or from post-operative swelling, both anticipated and unanticipated. Overall result is suture holes requiring less scar tissue to bridge the gap caused by unwanted widening or tearing either during placement or as post-penetration tension as placed on that site by the suture.

SUMMARY OF THE INVENTION

Accordingly, it is the object of the present invention to provide a surgical needle with an end to affix suture material, a rounded tapered surface along the inner circle side of the needle the entire distance along the shaft of the needle while on the outer side of the circle of the needle from the affixed suture end, a surf ace that will begin as a rounded surface extending into a cutting edge at a distance along the shaft that will ultimately end in a piercing point at the opposite end of the needle.

DETAILED DESCRIPTION OF THE DRAWINGS

FIG. 5 is a view of Section 20 in FIGS. 1-4 depicting suture material attachment to the surgical needle of the present invention.

FIG. 6 is a cross-sectional view taken in Section 40 of a surgical needle of the present invention.

FIG. 7 is a cross-sectional view taken in Section 50 of a surgical needle of the present invention.

FIG. 8 is a cross-view taken in Section 50 of a surgical needle of the present invention depicting needle placement orientation in relation to incision or wound edge.

DETAILED DESCRIPTION OF THE INVENTION

Figure 1:
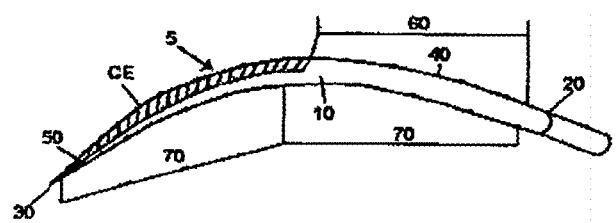
FIG. 1 is a perspective view of a surgical needle of the present invention having an improved cross-Sectional design.
Figure 2:
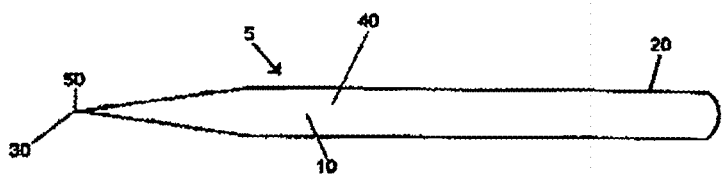
FIG. 2 is a top view of a needle of the present invention having an improved cross-sectional design.
Figure 3:
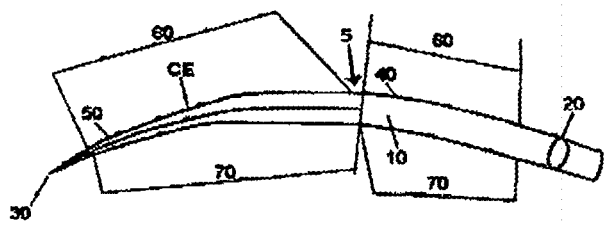
FIG. 3 is a side view of a needle of the present invention having an improved cross-sectional design.
Figure 4:
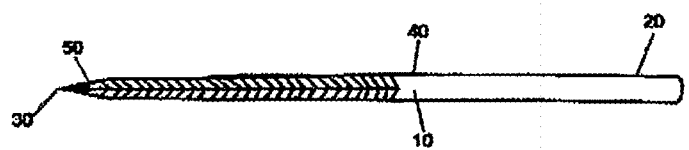
FIG. 4 is a bottom view of a needle of the present invention having an improved cross-sectional design.

As can be seen in FIGS. 1-4, the Surgical Needle 5 has an elongated shaft 10 having a Proximal Section 20, a Central Section 40, and a Distal Section 50. The Surgical Needle 5 terminates as an extremely sharp Piercing Point 30 on its distal end. Although FIG. 1 shows a conventional curvature of the Elongated Shaft 10, the configuration of the curvature may include straight, compound straight, and curved, with curvatures of ¼, ⅜, ½, or ⅝ as well as sections of Shaft 10 straight and curved both Top to Bottom and Side to Side. The Central Section 40 may include a roughened surface or cross-hatch pattern on the Shaft 10 for sufficient grasp of the Needle 5 by a surgical forceps or needle holder. In FIG. 5, the Proximal Section 20 of Needle 5 is seen as a circular configuration having a Central Suture Affixing Hole 25 that allows a Suture Material 200 to be securely mounted and swagged in place, the depth of the Hole 25 varies as needed to securely affix the suture, depending upon Suture Material 200 diameter and material make-up. Referring again to FIGS. 1, 3 the Needle 5 has a Central Section 40 of the Elongated Shaft 10 having no Cutting Edge CE on either its Upper Side 60 or Concave Lower Side 70. In FIG. 6 in Section 40, the cross-section of the Elongated Shaft 10 is rounded and made of solid surgical steel or other such material of desired tensile strength and hardness to prevent needle Elongated Shaft 10 bending or breaking of Surgical Needle 5 during tissue penetration of Piercing Point 30 and passage of Elongated Shaft 10 through dense tissue of the wound margin. Again referring to FIGS. 1-4 the Elongated Shaft 10 has a Distal Section 50 that is shown to originate as a gradual transformation from Section 40 and extends to and transforms into the extremely sharp Piercing Point 30. Although this transformation is shown in FIGS. 1-4 to be at a position approximately ⅜-⅝ the distance from Section 20 to Piercing Point 30 of the Surgical Needle 5, this transformation may be either abrupt or gradual and can occur at any point or region along the Elongated Shaft 10. The cross-section in Section 40 depicted in FIG. 6 as a round or nearly rounded transforms in Section 50 as seen in FIG. 7 and FIG. 8 as a tear drop shape configuration with the sharp end of the tear drop cross-section shape in FIG. 7 and FIG. 8 being an extremely sharp cutting edge CE as seen in FIG. 1 and FIG. 3. The opposite side of the Elongated Shaft 10 designated in FIG. 1 and FIG. 3 as Concave Lower Side 70 during the transformation from Section 40 to Section 50 and through the entire length of Section 50, however retains its rounded form, as depicted in Elongated Shaft 10 cross-section in FIG. 7 and FIG. 8 as the larger rounded portion of the tear drop on the Concave Lower Side 70 of the Elongated Shaft 10 in FIG. 1 and FIG. 3. In the case of straight or compound straight and curved configurations of the Elongated Shaft 10, the Cutting Edge CE as seen in cross-section in FIG. 7 and FIG. 8 of Distal Section 50 and seen as CE in FIG. 1 and FIG. 3 as extending the entire length of Section 50 will be placed on the Elongated Shaft 10 of the Surgical Needle 5 upon tissue penetration and entry by the Piercing Point 30 depicted in FIGS. 1-4 so as the Cutting Edge CE will be on the direct opposite side of the Elongated Shaft 10 and at a right angle, or perpendicular plane with the edge of the incision or wound edge W as seen in cross-section in FIG. 8. This would occur as a natural occurrence when placing the Piercing Point 30 of a curved Surgical Needle 5 as depicted in FIG. 1 and FIG. 3 and in cross-section in FIG. 8. In either instance the plane of the cut made by the Cutting Edge CE will be on the direct opposite side of the Elongated Shaft 10 from the edge of the Incision or Wound W being closed. As depicted in FIGS. 1-4 the distal end of Section 50 of the Elongated Shaft 10 continues to decrease in cross-section diameter beginning at the proximal end of Section 50 and continues to decrease until it becomes the Piercing Point 30 of the Needle 10. The exact distance from the termination of Section 50 to the tip of the Piercing Point 30 as shown in FIGS. 1-4 will necessarily vary with the size of the Surgical Needle 5 and the tensile strength of the material chosen for construction of the Surgical Needle 5. The final transition of Section 50 will however be a careful transition from Cutting Edge CE as shown in FIG. 7 and FIG. 8 to Piercing Point 30 as depicted in FIGS. 1-4 to allow maximum ease and exactness of tissue penetration by Piercing Point 30 while insuring ease of Surgical Needle 5 through both fragile and dense tissue.

The invention claimed is:

1. A curved surgical suture needle device comprising:
   an elongated shaft having a proximal section with a central suture affixing hole, a central portion, a distal section with a proximal portion and distal end, the distal section transitions from the distal end of the distal section to a tapered piercing point;
   the elongated shaft having an upper side and a concave lower side;
   the distal section having a rounded bottom surface extending along the concave lower side and two side surfaces extending up from the rounded bottom surface towards the upper side to form a single cutting edge at the upper side, the distal section has a tear drop shape cross section that extends the entire length of the distal section with the single cutting edge on the upper side that forms a tip of the tear drop shape cross section and the rounded surface on the concave lower side forming a bottom of the tear drop shape cross section, and the distal section having a cross sectional diameter continually decreasing from the proximal portion of the distal section to the distal end of the distal section;
   wherein the central section having a rounded cross section;
   wherein the tapered piercing point having a conical cross section;
   wherein the single cutting edge does not extend in the tapered piercing point, central portion and proximal section; and
   wherein the curved surgical suture needle is configured so that a plane of a cut made by the single cutting edge is on a direct opposite side of the elongated shaft from an edge of an incision being closed.

* * * * *